United States Patent [19]

Hsia et al.

[11] Patent Number: 4,898,717
[45] Date of Patent: Feb. 6, 1990

[54] MULTISTAGE PROCESS FOR CONVERTING OXYGENATES TO DISTILLATE HYDROCARBONS WITH INTERSTAGE ETHENE RECOVERY

[75] Inventors: Chung H. Hsia, Matawan; Hartley Owen, Belle Mead; Bernard S. Wright, East Windson, all of N.J.

[73] Assignee: Mobil Oil Corp., New York, N.Y.

[21] Appl. No.: 689,638

[22] Filed: Jan. 7, 1985

Related U.S. Application Data

[62] Division of Ser. No. 568,152, Jan. 4, 1984, Pat. No. 4,506,106.

[51] Int. Cl.$^4$ .............................. B01D 3/14; B01J 8/04
[52] U.S. Cl. .............................. 422/190; 203/DIG. 6; 422/187; 422/234; 422/235; 585/312; 585/322; 585/329; 585/469
[58] Field of Search ............... 585/312, 313, 322, 327, 585/329, 405, 469, 640, 533, 315, 402, 413, 415, 423, 424; 422/131, 134, 138, 234, 235, 187, 190; 203/DIG. 6

[56] References Cited

U.S. PATENT DOCUMENTS

| | | | |
|---|---|---|---|
| 2,939,834 | 6/1960 | Evans | 208/101 |
| 3,542,892 | 11/1970 | Stoker et al. | |
| 3,760,024 | 9/1973 | Cattanach | 585/415 |
| 4,021,502 | 5/1977 | Plank et al. | |
| 4,058,576 | 11/1977 | Chang et al. | 585/415 |
| 4,227,992 | 10/1980 | Garwood et al. | 208/46 |
| 4,433,185 | 2/1984 | Tabak | 585/312 |
| 4,444,988 | 4/1984 | Capsuto et al. | 585/415 |
| 4,450,311 | 5/1984 | Wright et al. | 585/415 |
| 4,456,779 | 6/1984 | Owen et al. | 585/415 |

Primary Examiner—Barry S. Richman
Assistant Examiner—Jill Johnston
Attorney, Agent, or Firm—Alexander J. McKillop; Charles J. Speciale; L. Gene Wise

[57] ABSTRACT

An integrated process is provided for converting methanol, dimethylether or the like to heavy hydrocarbon products, especially distillate range hydrocarbons. In a first stage catalytic process oxygenate feedstock is converted to lower olefins. $C_3+$ olefins are selectively sorbed in an interstage sorption fractionator and passed along with gasoline sorbent to a second stage oligomerization reactor. Distillate range hydrocarbons are useful as diesel fuel or the like.

7 Claims, 4 Drawing Sheets

MULTISTAGE PROCESS FOR CONVERTING OXYGENATES TO DISTILLATE HYDROCARBONS WITH INTERSTAGE ETHENE RECOVERY

CROSS-REFERENCE TO RELATED APPLICATION

This application is a division of copending U.S. patent application Ser. No. 568,152 filed Jan. 4, 1984, now U.S. Pat. No 4,506,106.

FIELD OF THE INVENTION

This invention relates to a system for converting organic oxygenates, such as methanol or dimethyl ether (DME), to liquid hydrocarbons. In particular it provides a continuous process for producing distillate range fuel products by dehydrating and converting the oxygemate feedstock catalytically to produce an intermediate lower olefinic stream, and oligomerizing a fraction of the olefins to produce a major amount of distillate product for use as diesel fuel or the like.

BACKGROUND OF THE INVENTION

Recent developments in zeolite catalysts and hydrocarbon conversion processes have created interest in utilizing olefinic feedstocks, for producing $C_5+$ gasoline, diesel fuel, etc. In addition to the basic work derived from ZSM-5 type zeolite catalysts, a number of discoveries have contributed to the development of a new industrial process, known as Mobil Olefins to Gasoline/Distillate ("MOGD"). This process has significance as a safe, environmentally acceptable technique for utilizing feedstocks that contain lower olefins, especially $C_2-C_5$ alkenes. This process may supplant conventional alkylation units. In U.S. Pat. Nos. 3,960,978 and 4,021,502, Plank, Rosinski and Givens disclose conversion of $C_2-C_5$ olefins, alone or in admixture with paraffinic components, into higher hydrocarbons over crystalline zeolites having controlled acidity. Garwood et al have also contributed improved processing techniques to the MOGD system, as in U.S. Pat. Nos. 4,150,062, 4,211,640 and 4,227,992. The above-identified disclosures are incorporated herein by reference.

Conversion of lower olefins, especially propene and butenes, over HZSM-5 is effective at moderately elevated temperatures and pressures. The conversion products are sought as liquid fuels, especially the $C_5+$ aliphatic and aromatic hydrocarbons. Olefinic gasoline is produced in good yield by the MOGD process and may be recovered as a product or recycled to the reactor system for further conversion to distillate-range products. Operating details for typical MOGD units are disclosed in copending U.S. Pat. No. 4,456,779 (Owen et al) and U.S. Pat. No. 4,433,185 (Tabak), incorporated herein by reference.

In addition to their use as shape selective oligomerization catalysts, the medium pore ZSM-5 type catalysts are useful for converting methanol and other lower aliphatic alcohols and/or corresponding ethers to olefins. Particular interest has been directed to a catalytic process for converting low cost methanol to valuable hydrocarbons rich in ethene and $C_3+$ alkenes. Various processes are described in U.S. Pat. Nos. 3,894,107 (Butter et al), 3,928,483 (Chang et al), 4,025,571 (Lago), and in copending U.S. patent application Ser. No. 388,768, filed June 15, 1982 (Yurchak et al), now abandoned. Significance of the methanol-to-olefins ("MTO") type processes, especially for producing ethene, is discussed in *Hydrocarbon Processing*, November 1982, pp. 117–120. It is generally known that the MTO process can be optimized to produce a major fraction of $C_2-C_4$ olefins.

SUMMARY OF THE INVENTION

It has been discovered that methanol, DME or the like may be converted to liquid fuels, particularly distillate, in a multi-stage continuous process, with a unique fractionation step between the major process conversion units.

In a preferred embodiment an integrated continuous system is provided for converting oxygenated organic feedstock to liquid hydrocarbons comprising methods and apparatus for contacting feedstock in a primary reactor stage with at least one catalyst comprising acidic zeolite at elevated temperature and moderate pressure to dehydrate and convert at least a portion of the feedstock to hydrocarbons containing a major fraction of $C_2-C_4$ olefins and a minor fraction containing $C_5+$ heavy hydrocarbon. After cooling and separating primary stage effluent to provide an aqueous liquid stream, a heavy hydrocarbon liquid stream and a light hydrocarbon vapor stream rich in $C_2-C_4$ olefins, the light hydrocarbon stream is fractionated by selectively sorbing $C_3+$ hydrocarbons in a gasoline sorbent stream to recover an ethene-rich vapor stream and a liquid stream rich in $C_3+$ sorbate. In a secondary reactor stage the sorbate-rich stream is contacted with oligomerization catalyst comprising medium-pore shape selective acidic zeolite at substantially increased pressure and elevated temperature to convert olefins to a heavier liquid hydrocarbon effluent stream comprising olefinic gasoline and distillate range liquids. The liquid hydrocarbon effluent stream from the secondary stage is fractionated to obtain a distillate stream, gasoline stream and lighter hydrocarbon stream, at least a portion of the gasoline stream is recycled as sorbent. The oligomerization catalyst preferably comprises ZSM-5 type zeolite.

Other objects and features of the invention will be seen in the following description and drawings.

THE DRAWINGS

DESCRIPTION OF PREFERRED EMBODIMENTS

Catalyst versatility permits the same zeolite to be used in both the primary stage (MTO) and secondary oligomerization stage (MOGD). While it is within the inventive concept to employ substantially different catalysts in these stages, it is advantageous to employ a standard ZSM-5 having a silica alumina molar ratio of 70:1.

The oligomerization catalysts preferred for use herein include the medium pore shape selective crystalline aluminosilicate zeolites having a silica to alumina ratio of at least 12, a constraint index of about 1 to 12 and acid cracking activity of about 160-200. Representative of the ZSM-5 type zeolites are ZSM-5, ZSM-11, ZSM-12, ZSM-22, ZSM-23, ZSM-35 and ZSM-38. ZSM-5 is disclosed in U.S. Pat. No. 3,702,886 and U.S. Pat. No. Re. 29,948. Other suitable zeolites are disclosed in U.S. Pat. Nos. 3,709,979; 3,832,449, 4,076,979, 3,832,449, 4,076,842, 4,016,245 and 4,046,839. The disclosures of these patents are incorporated herein by reference. A suitable catalyst for each fixed bed operation consisting essentially of HZSM-5 zeolite with 35 wt.% alumina binder in the form of cyclindrical extrudates of about 1-5 mm diameter. Other catalysts which may be employed for converting methanol/DME to lower olefins include the borosilicate, ferrosilicate, "silicalite" and/or synthetic mordenite materials.

In this description, metric units and parts by weight are employed unless otherwise stated. While various reactor configurations may be used, including fluidized bed catalytic reactors, moving bed and fixed bed reactors, the invention is described for use in a plurality of fixed bed reactors operated under differeing process conditions depending upon relative position in the system.

Figure 1:
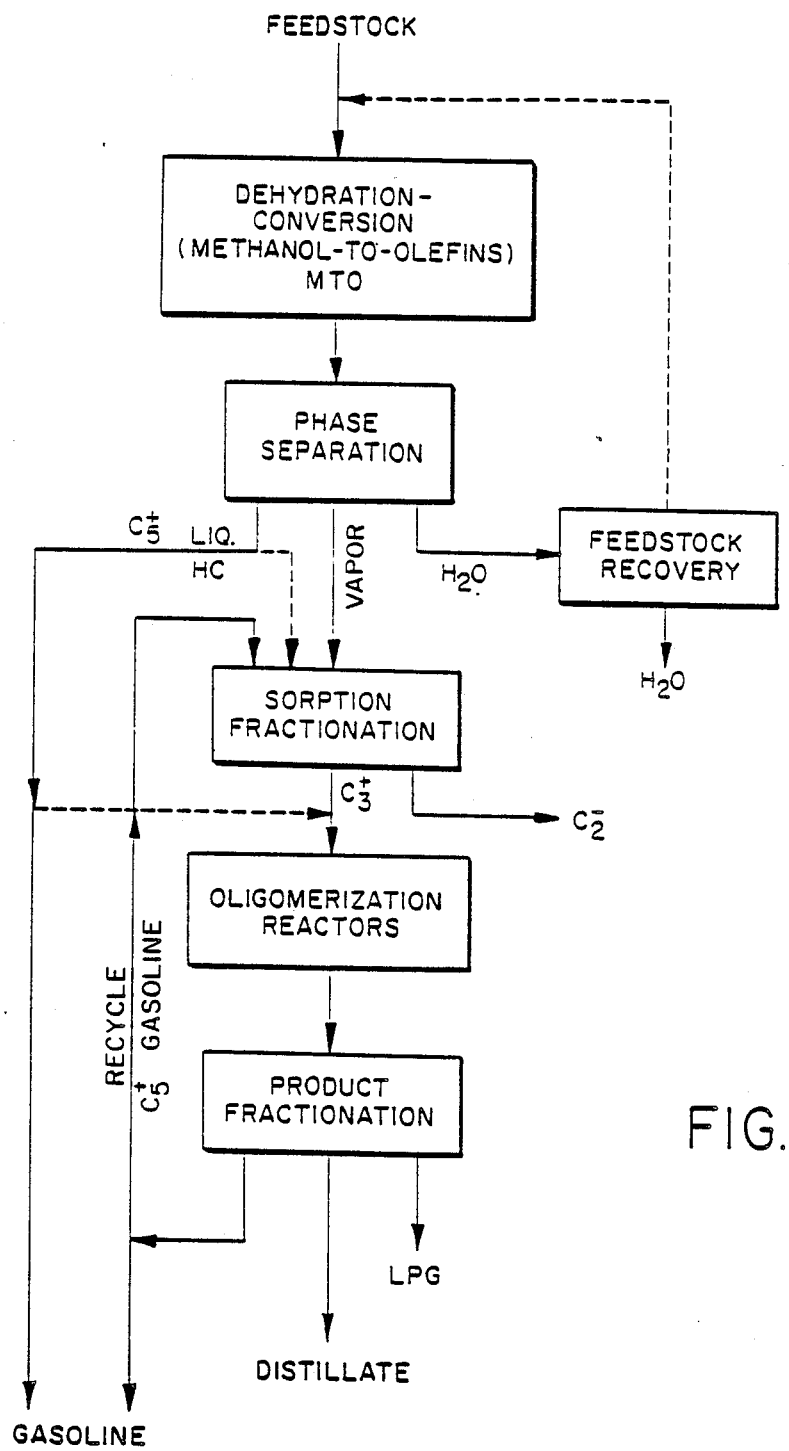
FIG. 1 is a process flow sheet showing the major unit operations and process streams.

Referring to FIG. 1, oxygenate feedstock (methanol or DME, for instance) is fed to the primary stage where it is converted to a lower olefin and heavier hydrocarbon plus water by dehydration of the oxygenated feedstock. Byproduct water is recovered by simple phase separation from the cooled effluent. Liquid hydrocarbons (HC) comprising $C_5+$ gasoline range materials may be recovered or, optionally combined with the lower olefinic vapor for further conversion in the secondary stage. The olefinic vapor phase effluent from the primary stage is then contacted with a gasoline sorbent stream in the sorption fractionation section to provide a $C_3+$ liquid stream, which is passed to the oligomerization reaction section. The combined olefinic stream (containing recycled olefinic gasoline rich in $C_3$-$C_4$ olefin sorbate) is reacted at high pressure and elevated temperature over the oligomerization catalyst. Secondary stage effluent is then separated into light gases, $C_5+$ gasoline for recycle and distillate range hydrocarbons. The distillate stream contains a major fraction of high boiling aliphatics and a minor amount of aromatics. The distillate product may be further stabilized by hydrotreating (HDT) in a relatively mild process to saturate the olefinic compounds and convert aromatics to corresponding naphthenes without substantial cracking or dealkylation to yield a distillate fuel product. Ethylene (ethene, $C_2H_2$) is recovered as a valuable chemical feedstock from the process.

In the process for catalytic conversion of olefins to heavier hydrocarbons by catalytic oligomerization using an acid crystalline zeolite, such as ZSM-5 type catalyst, process conditions can be varied to favor the formation of either gasoline or distillate range products. At moderate temperature and relatively high pressure, the conversion conditions favor distillate range product having a normal boiling point of at least 165° C. (330° F.). Lower olefinic feedstocks containing $C_2$-$C_6$ alkenes may be converted selectively; however, the distillate mode conditions do not convert a major fraction of ethylene. While propene, butene-1 and others may be converted to the extent of 50 to 95% in the distillate mode, only about 10 to 50% of the ethylene component will be consumed. Accordingly, the ethene is advantageously recovered prior to the oligomerization stage.

Figure 2:
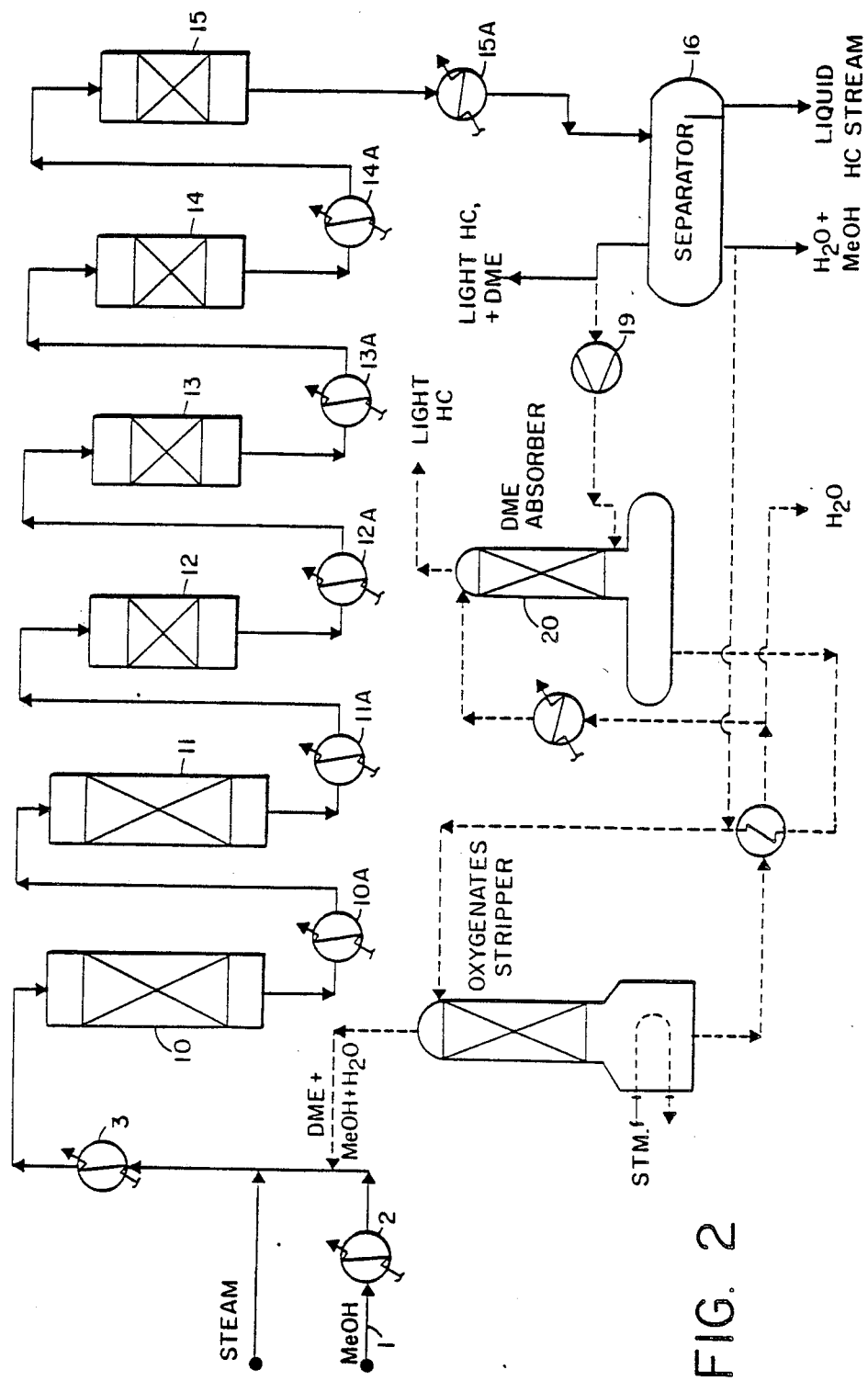
FIG. 2 is a schematic representation of a preferred multireactor system and fractionation system for dehydration and conversion of methanol and/or DME to lower olefins.

Primary stage conversion operation in FIG. 2 depicts a fixed bed multi-reactor system for converting methanol ($CH_3OH$) and/or DME. A typical crude methanol feedstock may contain 4 to 17% water, with minor amounts of carbon oxides, methane, DME, etc.

In the primary stage, ethene production may be optimized by employing fixed bed primary stage conditions in the temperature range of about 260° C. to 425° C., a pressure range of about 170 to 800 kPa and weight hourly space velocity range of about 0.5 to 1.0 based on ZSM-5 equivalent catalyst and methanol equivalent in the primary stage feedstock. Typically about 25 to 90% of MeOH/DME feedstock is converted per reactor pass and water diluent is cofed with methanol and/or dimethyl ether in a molar ratio of about 0.1:1 to 5:1. Under these conditions, the primary stage hydrocarbon effluent usually contains about 25 to 40 wt.% ethene, about 10 to 50 wt.% propene, about 2 to 30 wt.% butene, less than 10 wt.% $C_1$ to $C_4$ paraffins, and about 5 to 20 wt.% aromatics, including about 1 to 5 wt.% durene.

In the preferred embodiment of FIG. 2, the feedstock is methanol (MeOH), which may be partially dehydrated in a separate process step over gamma-alumina catalyst to yield dimethyl ether (DME) and water. A preliminary dewatering step can be used to provide a feedstock consisting essentially of MeOH and/or DME; however, the presence of water in the MTO reactor may be beneficial. The feedstock is fed continuously under low pressure through line 1 and heat exchanger 2, where it is raised to process temperature, and introduced to the first stage MTO reactor system. The initial dehydration reactor 10 is followed by a series of fixed bed catalytic reactors 11, 12, 13, 14 and 15 containing zeolite conversion catalyst. Inter-reactor coolers 10A, 11A, 12A, 13A, 14A and effluent cooler 15A control temperature of the process stream. Interstage separation means is provided for recovering water and hydrocarbons from the primary stage effluent stream. The first stage effluent is cooled to condense water and a major amount of $C_5+$ liquid hydrocarbons. These liquids are separated from the hydrocarbon vapor in phase separator means 16. Byproduct water may be recovered from unreacted feedstock and discarded, or optionally a portion may be recycled, as indicated by the dashed lines. The liquid hydrocarbon phase and the ethene-rich light hydrocarbon vapor streams are recovered from separator 16. Optionally unconverted DME may be removed by absorber 20. This optional section includes a compressor 19 and stripper 21. Other suitable fixed bed catalytic processes for conversion of methanol/DME to lower olefins are described in U.S. Pat. Nos. 4,387,263, 4,393,265, 4,361,715 and South African Patent Application Ref. No. V01750 (Clover et al) filed Mar. 30, 1983, the entire disclosures of which are incorporated herein by reference. While the primary stage dehydration reactor has been exemplified herein by a fixed bed unit, a suitable fluid catalyst apparatus is disclosed in U.S. Pat. No. 4,379,123 (Daviduk and Haddad).

A typical MTO operation is conducted over a fixed bed of small crystal (0.02-0.05μ) HZSM-5/alumina extrudate catalyst at about 170 kPa (25 psia), with a 1:1 $H_2O:CH_3OH$ equivalent ratio at 315° C. (600° F.) at a space velocity (WHSV=0.5-1) to convert about 50% of the oxygenated organic feedstock components to hydrocarbons. Table I lists the organic hydrocarbon product distribution from a typical MTO process.

TABLE I

| MTO Product Distribution | |
|---|---|
| Component | wt. % |
| Methane, wt. % | 0.6 |
| Ethylene, wt. % | 26.2 |
| Ethane, wt. % | 0.1 |
| Propylene, wt. % | 22.8 |
| Propane | 3.9 |
| Butenes | 7.9 |
| Isobutane | 3.9 |
| n-Butane | 2.6 |
| Pentenes | 2.4 |
| $C_5 P + N$ | 7.1 |
| $C_6 P + N$ | 5.1 |
| $C_7 O$ | 0.6 |
| $C_7 P + N$ | 3.2 |
| $C_7 O$ | 0.7 |
| $C_8 P + O + N$ | 2.1 |
| $C_9 P + O + N$ | 1.3 |
| $C_{10} P + O + N$ | 1.1 |
| Benzene | 0.1 |
| Toluene | 0.5 |
| $C_8$ Aromatics | 3.5 |
| $C_9$ Aromatics | 2.1 |
| $C_{10}$ Aromatics | 2.2 |
| (Durene) | (1.7) |

SORPTION FRACTIONATION

The light hydrocarbon stream recovered from the primary conversion stage preferably contains a major amount of $C_2$-$C_4$ olefins. The novel system includes a first fractionation means for recovering ethene from the primary stage olefinic vapor including a sorption tower operatively connected to selectively sorb $C_3+$ hydrocarbons from the olefinic vapor in a liquid sorption stream. Since the interstage fractionation unit is usually operated at a pressure higher than the primary stage and lower than the secondary conversion stage, vapor compression means for the primary stage light hydrocarbon stream and means for pressurizing and heating the liquid sorption stream containing $C_3+$ sorbate are provided.

A suitable sorption fractionation system is described in copending U.S. patent application Ser. No. 508,779 filed June 29, 1983 (Hsia et al now U.S. Pat. No. 4,479,812), the disclosure of which is incorporated herein by reference. The $C_2-$ and $C_3+$ separation is accomplished by a single absorber-stripper using gasoline recycle as absorbent and pumparounds for removing absorption heat. The amount of absorbent is set by the amount of recycle gasoline required in the $C_3+$ olefins conversion reaction thereby allowing the tower bottom stream to be pumped directly to the reactor pressure. Without using refrigeration, this tower efficiently and effectively separates the ethylene and light gases ($H_2$, CO, $CO_2$ and $CH_4$) from the $C_3+$ hydrocarbon.

The gasoline sorbent is an aliphatic hydrocarbon mixture boiling in the normal gasoline range of about 50° to 165° C. (125° to 330° F.), with minor amounts of $C_4$-$C_5$ alkanes and alkenes. Preferably, the total gasoline sorbent stream to feedstock weight ratio is greater than about 3:1; however, the content of $C_3+$ olefinic components in the feedstock is a more preferred measure of sorbate to sorbent ratio. Accordingly, the process may be operated with a mole ratio of about 0.2 moles to about 10 moles of gasoline per mole of $C_3+$ hydrocarbons in the feedstock, with optimum operation utilizing a sorbent:sorbate molar ratio about 1:1 to 1.5:1.

It is understood that the various process conditions are given for a continuous system operating at steady state, and that substantial variations in the process are possible within the inventive concept. In the detailed examples, metric units and parts by weight are employed unless otherwise specified.

Figure 3:
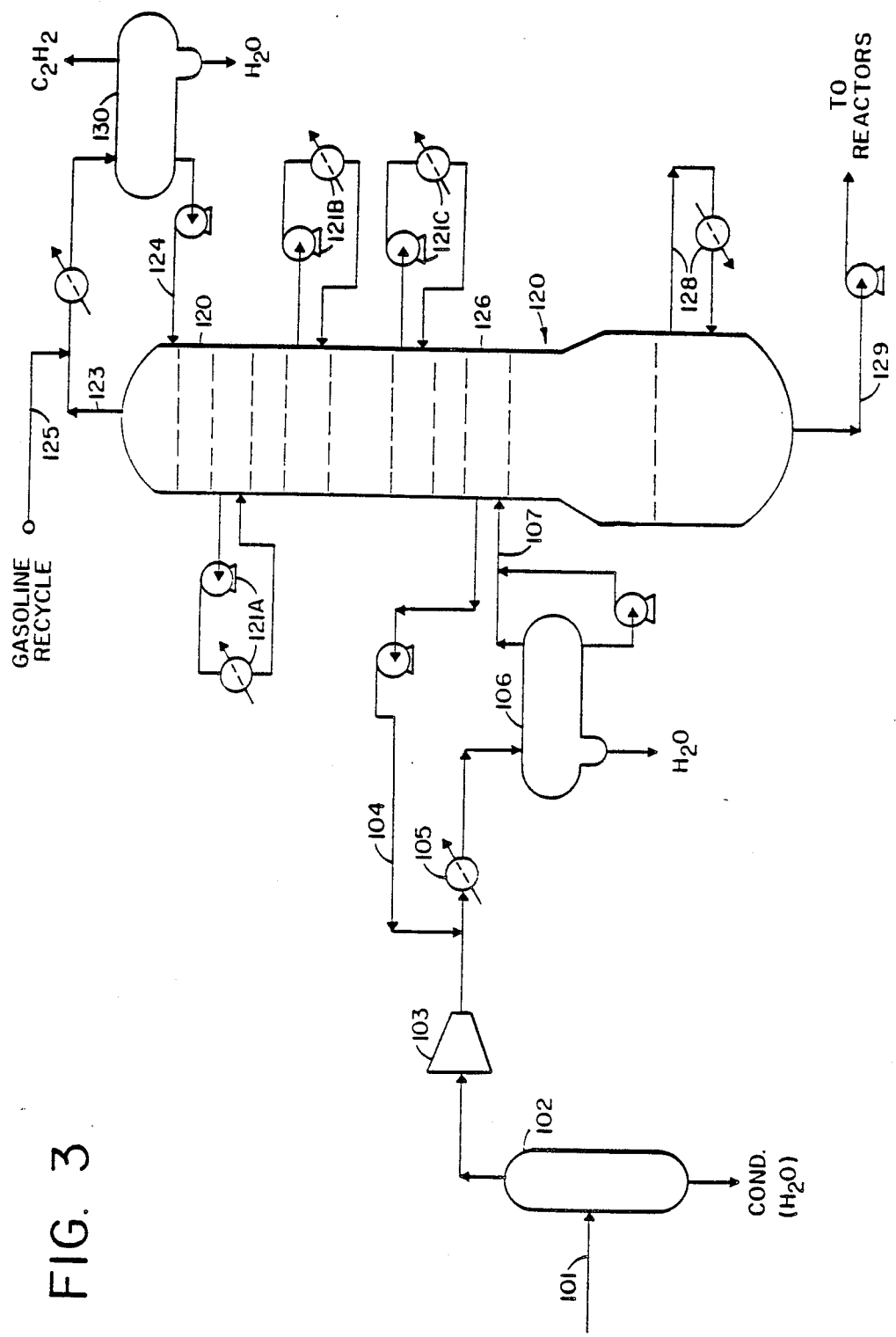
FIG. 3 is a preferred sorption fractionation system.

Referring to FIG. 3 of the drawing, olefinic feedstock is introduced to the system through a feedstock inlet 101, passing through knockout pot 102 to remove any condensate, such as water. At this point the vapor is at a temperature from ambient up to about 38° C. (100° F.) and a pressure of about 60 kPa (75 psig), and is pressurized by compressor means 103 to about 2230 kPa (310 psig). This pressurized stream is then mixed with a liquid downcomer stream 104 from fractionating tower 120, cooled in exchanger 105 to about 35°–40° C. and passed to phase separator 106 where condensed water is removed. The hydrocarbon stream is then fed via conduit 107 connected between stages of fractionating sorption tower 120 wherein gaseous olefinic feedstock is contacted with liquid sorbent in a vertical fractionation column operating at least in the upper portion thereof in countercurrent flow. Effectively this unit is a $C_2/C_3+$ splitter. The sorption tower employs a plate column; however, the fractionation equipment may employ vapor-liquid contact means of various designs in each stage including packed beds of Raschig rings, saddles or other porous solids or low pressure drop contact devices.

Sorption tower 120, as depicted, has multiple contact zones, with the heat of absorption being removed via interstage pump around cooling means 121A, B, and C. The liquid gasoline sorbent is introduced to the sorption tower through an upper inlet means 125 above the top contact section 120T. It is preferred to mix incoming liquid sorbent with outgoing splitter overhead ethylene-rich gas. High purity ethylene is recovered from the system through gas outlet 131 and sent to storage, further processing or conversion to other products. Liquid sorbent from separator 130 is then pumped to the upper liquid inlet 124 for countercurrent contact in a plate column or the like with upwardly flowing ethylene rich vapors. Liquid from the bottom of upper contact zone is pumped to a heat exchanger in loop 121A, cooled and returned to the tower in loop 121B adjacent an intermediate contact zone, again cooled in loop 121C, and returned to the tower above contact zone 126, which is located at the feedstock inlet 1. Under tower design conditions of about 2060 kPa (300 psia), it is preferred to maintain liquid temperature of streams entering the tower from 121, 122 and 124 at about 40° C. (100° F.). The lower contact zone provides further fractionation of the olefin-rich liquid. Heat is supplied to the sorption tower by removing liquid from the bottom via reboiler loop 128, heating this stream in a heat exchanger, and returning the reboiled bottom stream to the tower below contact zone 126. The liquid sorbate-sorbent mixture is withdrawn through bottom outlet 129 and pumped to storage or directly to the secondary stage for further reaction. The fractionator bottoms stream 129 is recovered at about 120° C. (250° F.), then pumped to the higher reactor pressure (e.g., about 4670 kPa, 665 psig) and passed to the secondary conversion stage. A typical sorption fractionation material balance is given below, for steady state operation using olefinic feed gas from the MTO primary stage. The units are expressed in moles per hour.

TABLE II

SORPTION FRACTIONATION MATERIAL BALANCE

| | FEED GAS | RECYCLE GASOLINE | GAS PRODUCT STREAM | LIQUID SORBATE STREAM |
|---|---|---|---|---|
| $H_2$ | 1.17 | — | 1.17 | — |
| CO | 0.22 | — | 0.22 | — |
| $CO_2$ | 0.38 | — | 0.38 | — |
| $C_1$ | 0.63 | — | 0.63 | — |
| $C_2$ | 14.83 | — | 14.78 | 0.05 |
| $C_2$ | 0.11 | — | 0.10 | 0.01 |
| $C_3$ | 8.09 | — | 0.36 | 7.73 |
| $C_3$ | 1.62 | — | 0.02 | 1.60 |
| $iC_4$ | 1.00 | 0.09 | 0.03 | 1.06 |
| $C_4$ | 2.40 | 0.03 | 0.01 | 2.42 |
| $nC_4$ | 0.32 | 0.17 | 0.04 | 0.45 |
| $iC_5$ | 0.67 | 2.64 | 0.25 | 3.06 |
| $C_5$ | 0.24 | 1.23 | 0.11 | 1.36 |
| $nC_5$ | 0.06 | 0.22 | 0.02 | 0.26 |
| $C_6$ | 0.81 | 11.19 | 0.13 | 11.87 |
| $H_2O$ | 0.37 | — | 0.03 | — |
| | 32.92 | 15.58 | 18.27 | 29.88 |

SECONDARY STAGE

Oligomerization Reactor Operation

The secondary stage provides catalytic oligomerization reactor means containing medium pore shape selective zeolite oligomerization catalyst for converting olefinic hydrocarbons in the sorption stream to liquid hydrocarbons comprising a major amount of distillate. This process stream is passed to second fractionation means for separating secondary stage effluent into a light hydrocarbon stream rich in LPG ($C_3$-$C_4$) aliphatic hydrocarbons, a $C_5$+ gasoline stream and distillate range stream. Means is provided for recycling at least a portion of the $C_5$+ gasoline stream to the first sorption fractionation means as a lean sorbent stream.

Figure 4:
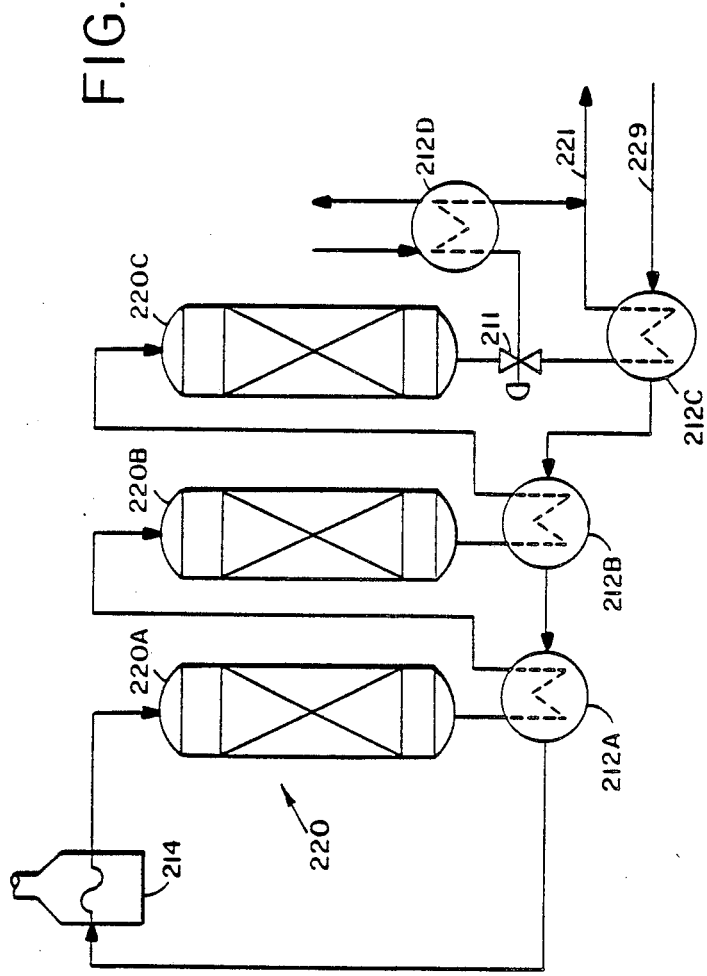
FIG. 4 is a typical olefin conversion reactor system for distillate mode operation.

A typical distillate mode secondary stage reactor system 220 is shown in FIG. 4. A plural reactor system may be employed with inter-reactor cooling, whereby the reaction exotherm can be carefully controlled to prevent excessive temperature above the normal moderate range of about 190° to 315° (375°-600° F.). The olefinic feedstream comprising the $C_3$+ light hydrocarbons and sorbent gasoline is introduced through conduit 229 and carried by a series of conduits through heat exchangers 212A, B, C and furnace 214 where the feedstream is heated to reaction temperature. The olefinic feedstream is then carried sequentially through a series of zeolite beds 220A, B, C wherein at least a portion of the olefin content is converted to heavier distillate constituents. Advantageously, the maximum temperature differential across only one reactor is about 30° C. ($\Delta T \sim 50°$ F.) and the space velocity (LHSV based on olefin feed) is about 0.5 to 1.5. The heat exchangers 212A and 212B provide inter-reactor cooling and 212C reduces the effluent to separation temperature. An optional heat exchanger 212D may further recover heat from the effluent stream 121 prior to separation.

Preferably, the secondary stage process conditions are optimized to produce heavy liquid hydrocarbons having a normal boiling above 165° C. (330° F.) are fed as a continuous stream to a final fractionator unit (such as a distillation system). Gasoline, rich in $C_5$+ olefins and lighter hydrocarbons are fractionated in a tower to provide an olefinic gasoline stream for recycle to the MOGD reactor system or recovered as product. The lighter hydrocarbons, rich in $C_3$-$C_4$ alkenes may be condensed and recovered as LPG product or optionally recycled to the MOGD reactor system. The secondary stage typical HZSM-5 fixed bed reactor system depicted in FIG. 4, operates at 0.6 liquid hourly space velocity (based on olefins fed to reactors), 1:1 gasoline-:olefin recycle ratio, temperature of 230° C. (450° F.) (SOC) to 315° C. (600° F.) (EOC) and a total pressure of 4225 kPa (600 psig) at minimum olefin partial pressure at the inlet of 1100 kPa (160 psig). The secondary stage effluent from such a typical system is shown below.

TABLE III

| Component | Wt. % |
|---|---|
| $CH_4$ | 0.07 |
| $C_2H_6$ | 0.13 |
| $C_3H_8$ | 2.80 |
| $IC_4H_{10}$ | 2.00 |
| $NC_4H_{10}$ | 2.00 |
| $i$-$C_5H_{12}$ | 0.42 |
| $n$-$C_5H_{12}$ | 0.03 |
| $C_5H_{10}$ | 0.95 |
| $C_6$ — 330°(Gasoline) | 12.60 |
| 330° + (Distillate) | 79.00 |

A typical MOGD secondary stage fractionation system is described in copending U.S. patent application Ser. No. 488,834 filed Apr. 26, 1983 (Owen et al), incorporated herein by reference.

It is within the inventive concept to cascade substantially all $C_3$+ vapor and liquid hydrocarbon first stage product into an MOGD reactor followed by hydrotreating of the distillate product as depicted in the dashed lines of FIG. 1. This will minimize the number of process steps and will maximize distillate production by polymerizing gasoline range olefins, and by alkylating gasoline range aromatics. Durene can be reduced via saturation to its corresponding naphthene in a subsequent mild hydrotreating step. Substantially all of the polymethylbenzenes or other aromatics formed in the dehydration reactor stage can be accumulated in the distillate fraction according to the present invention, and hydrotreated distillate durene content is decreased substantially below 2 wt.%, preferrably below 1%.

The present process is particularly useful in producing a major product stream wherein the 165 $C$+ fraction consists mainly of $C_{10}$ to $C_{20}$ aliphatic hydrocarbons containing a minor amount of cyclic components. The low temperature, high pressure distillate mode secondary stage operation favors the formation of linear oligomers. The preferred distillate mode operation can provide a larger part of the total (non-ethene) fuel products as heavy hydrocarbons, while retaining a high yield of valuable ethene product.

We claim:

1. A continuous multi-stage catalytic system for converting oxygenated feedstock to liquid hydrocarbons comprising primary stage catalytic dehydration means containing catalyst for converting oxygenate to light olefinic vapor and normally liquid $C_5$+ hydrocarbons;
   interstage separation means for recovering water and hydrocarbons from the primary stage effluent stream;
   first fractionation means for recovering ethene from the primary stage olefinic vapor including a sorption tower operatively connected to selectively sorb $C_3$+ hydrocarbons from the olefinic vapor in a liquid sorption stream;
   means for pressurizing and heating the liquid sorption stream containing $C_3$+ sorbate;

secondary stage catalytic oligomerization reactor means containing medium pore shape selective zeolite oligomerization catalyst for converting olefinic hydrocarbons in the sorption stream to liquid hydrocarbons comprising a major amount of distillate;

second fractionation means for separating secondary stage effluent into a light hydrocarbon stream rich in $C_3$-$C_4$ aliphatic hydrocarbons, a $C_5+$ gasoline stream and distillate range stream; and means for recycling at least a portion of the $C_5+$ gasoline stream to the first fractionation means as a lean sorbent stream.

2. The system of claim 1 comprising means for contacting an ethylene rich gaseous stream from the first fractionation means with a minor amount of heavy liquid absorbent to provide a purified ethylene product.

3. An integrated continuous system for converting oxygenated organic feedstock to liquid hydrocarbons comprising, in combination:

a primary reactor stage having means for contacting feedstock having with at least one catalyst comprising acidic zeolite catalyst at elevated temperature and moderate pressure convert at least a portion of the feedstock to hydrocarbons containing a major fraction of $C_2$-$C_4$ olefins and a minor fraction containing $C_5+$ heavy hydrocarbons;

means for cooling and separating primary stage effluent to provide an aqueous liquid stream, a heavy hydrocarbon liquid stream and a light hydrocarbon vapor stream rich in $C_2$-$C_4$ olefins;

fractionation means for selectively sorbing $C_3+$ hydrocarbons from the light hydrocarbon stream in a gasoline sorbent stream to recover an ethene-rich vapor stream and a liquid stream rich in $C_3+$ sorbate;

a secondary reactor stage having means for contacting the sorbate-rich stream with oligomerization catalyst comprising medium-pore shape selective acidic zeolite at substantially increased pressure and elevated temperature to convert olefins to a heavier liquid hydrocarbon effluent stream comprising olefinic gasoline and distillate range liquids;

means for fractionating the liquid hydrocarbon effluent stream from the secondary stage to obtain a distillate stream, gasoline stream and lighter hydrocarbon stream;

and means for recycling at least a portion of the gasoline stream as sorbent.

4. The system of claim 3 wherein the oligomerization catalyst comprises HZSM-5 type zeolite.

5. The system of claim 3 wherein the secondary stage contains a fixed bed of shape selective medium pore zeolite catalyst to oligomerize olefins, said zeolite having a silica:alumina molar ratio greater than about 12:1 and a constraint index of about 1 to 12.

6. The system of claim 3 comprising a fixed bed primary stage having means for maintaining conditions in the temperature range of about 260° C. to 425° C., a pressure range of about 170 to 800 kPa and weight hourly space velocity range of about 0.5 to 1.0 based on ZSM-5 equivalent catalyst and methanol equivalent in the primary stage feedstock.

7. An integrated continuous system for converting methanol feedstock to liquid hydrocarbons comprising a primary reactor stage having means for contacting feedstock with zeolite methanol conversion catalyst at elevated temperature and moderate pressure to convert at least a portion of the feedstock to light hydrocarbons comprising $C_2$-$C_4$ olefins and by-product water;

means for cooling and phase separating primary stage effluent to provide an aqueous liquid phase and a light hydrocarbon vapor stream rich in $C_2$-$C_4$ olefins;

a sorption unit operatively connected between conversion stages for recovering ethene from the light hydrocarbon vapor stream, comprising a gas-liquid contact tower having an upper liquid sorbent inlet means for supplying recycled sorbent, vapor inlet means, lower liquid outlet means for recovering a liquid stream rich in $C_3+$ sorbate, and upper gas outlet means for unabsorbed ethene-rich vapors;

pump means for pressurizing the liquid sorbate stream;

a secondary reactor stage having means for contacting the sorbate-rich stream with oligomerization catalyst comprising medium-pore shape selective acidic zeolite at high pressure and elevated temperature to convert olefins to a heavier liquid hydrocarbon effluent stream consisting essentially of olefinic liquids and rich in distillate; and means for recycling a $C_6+$ fraction of the olefinic liquid effluent stream as sorbent.

* * * * *